United States Patent
Wyrick et al.

(10) Patent No.: US 12,209,108 B2
(45) Date of Patent: Jan. 28, 2025

(54) METHOD AND MEANS FOR AN ISOLATION OF MEMBRANE-BOUND PROTEINS FROM A BIOLOGICAL SAMPLE, PREFERABLY PROCESSED PLANT SEED MEAL

(71) Applicant: BASF PLANT SCIENCE COMPANY GMBH, Ludwigshafen (DE)

(72) Inventors: Meghan K. Wyrick, Research Triangle, NC (US); Min Xia, Research Triangle, NC (US); Janna Slessareva, Research Triangle, NC (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 483 days.

(21) Appl. No.: 16/956,058

(22) PCT Filed: Dec. 12, 2018

(86) PCT No.: PCT/EP2018/084551
§ 371 (c)(1),
(2) Date: Jun. 19, 2020

(87) PCT Pub. No.: WO2019/121235
PCT Pub. Date: Jun. 27, 2019

(65) Prior Publication Data
US 2020/0369717 A1    Nov. 26, 2020

(30) Foreign Application Priority Data
Dec. 22, 2017   (EP) ..................................... 17210241

(51) Int. Cl.
*C07K 1/36*    (2006.01)
*A23J 1/00*    (2006.01)
(Continued)

(52) U.S. Cl.
CPC ............... *C07K 1/145* (2013.01); *A23J 1/005* (2013.01); *A23J 1/006* (2013.01); *A23J 3/16* (2013.01); *C07K 1/36* (2013.01)

(58) Field of Classification Search
CPC .. C07K 1/145; C07K 1/36; A23J 1/005; A23J 1/006; A23J 3/16
(Continued)

(56) References Cited

U.S. PATENT DOCUMENTS

2003/0060607 A1 * 3/2003 Diosady ................ A23L 33/185
530/372
2006/0031959 A1 * 2/2006 Falco ................... C12N 9/0051
536/23.6
(Continued)

FOREIGN PATENT DOCUMENTS

WO    WO-0032790 A2 *  6/2000    ........... C12N 9/0083

OTHER PUBLICATIONS

Madduri, K. M. et al. Food and Chem. Toxicol. 50: 3776-3784 (Year: 2012).*
(Continued)

*Primary Examiner* — Hamid R Badr
(74) *Attorney, Agent, or Firm* — MARSHALL, GERSTEIN & BORUN LLP

(57) ABSTRACT

The present invention provides the method and means for an efficient isolation of membrane-bound proteins from biological samples, e.g. in samples from raw or processed plant material, preferably defatted plant seed meal such as canola meal. The biological sample can be highly processed, e.g. by applying high temperature, pressure, or a chemical treatment and can be derived from seed matrices as well as other typical plant tissues for example seed, grain, leaf, root, or pollen. The invention comprises the provision of a novel extraction buffer (MEB) and its application in the method of
(Continued)

the invention, wherein the buffer has a strong alkaline pH of 10 to 12.5 and comprises a soluble concentration of detergent at a level of 0.5% to 5%.

24 Claims, 6 Drawing Sheets

(51) Int. Cl.
  *A23J 3/16* (2006.01)
  *C07K 1/14* (2006.01)
(58) Field of Classification Search
  USPC .................................................... 530/370
  See application file for complete search history.

(56) References Cited

U.S. PATENT DOCUMENTS

| | | | |
|---|---|---|---|
| 2006/0117413 A1* | 6/2006 | Hildebrand | C12N 15/821 800/312 |
| 2006/0218669 A1* | 9/2006 | Joshi | C07K 14/415 530/370 |
| 2009/0123910 A1* | 5/2009 | Malick | C12N 15/52 435/5 |
| 2014/0024714 A1 | 1/2014 | Wijesundera et al. | |

OTHER PUBLICATIONS

Bach, T. J. et al. Eur. J. Biochem. 154 : 103-111 (Year: 1986).*
"Step in Oil and meal Processing", Canola Council of Canada, retrieved on Jul. 16, 2020, 3 pages. (Available at: https://www.canolacouncil.org/oil-and-meal/what-is-canola/how-canola-is-processed/steps-in-oil-and-meal-processing/#Pressing).
European Search Report for EP Patent Application No. 17210241.0, Issued on Jun. 21, 2018, 4 pages.
Gerzhova, et al., "Study of total dry matter and protein extraction from canola meal as affected by the pH, salt addition and use of zeta-potential/turbidimetry analysis to optimize the extraction conditions", Food Chemistry, vol. 201, Jun. 15, 2016, pp. 243-252.
Klockeman, et al., "Isolation and Characterization of Defatted Canola Meal Protein", Journal of Agricultural and Food Chemistry, vol. 45, Issue 10, Oct. 15, 1997, pp. 3867-3870.
Cesur et al., The Subcellular Localisation of the Human Papillomavirus (HPV) 16 E7 Protein in Cervical Cancer Cells and Its Perturbation by RNA Aptamers, Viruses, 7(7):3443-61 (2015).
International Application No. PCT/EP2018/084551, International Search Report and Written Opinion, mailed Feb. 11, 2019.

* cited by examiner

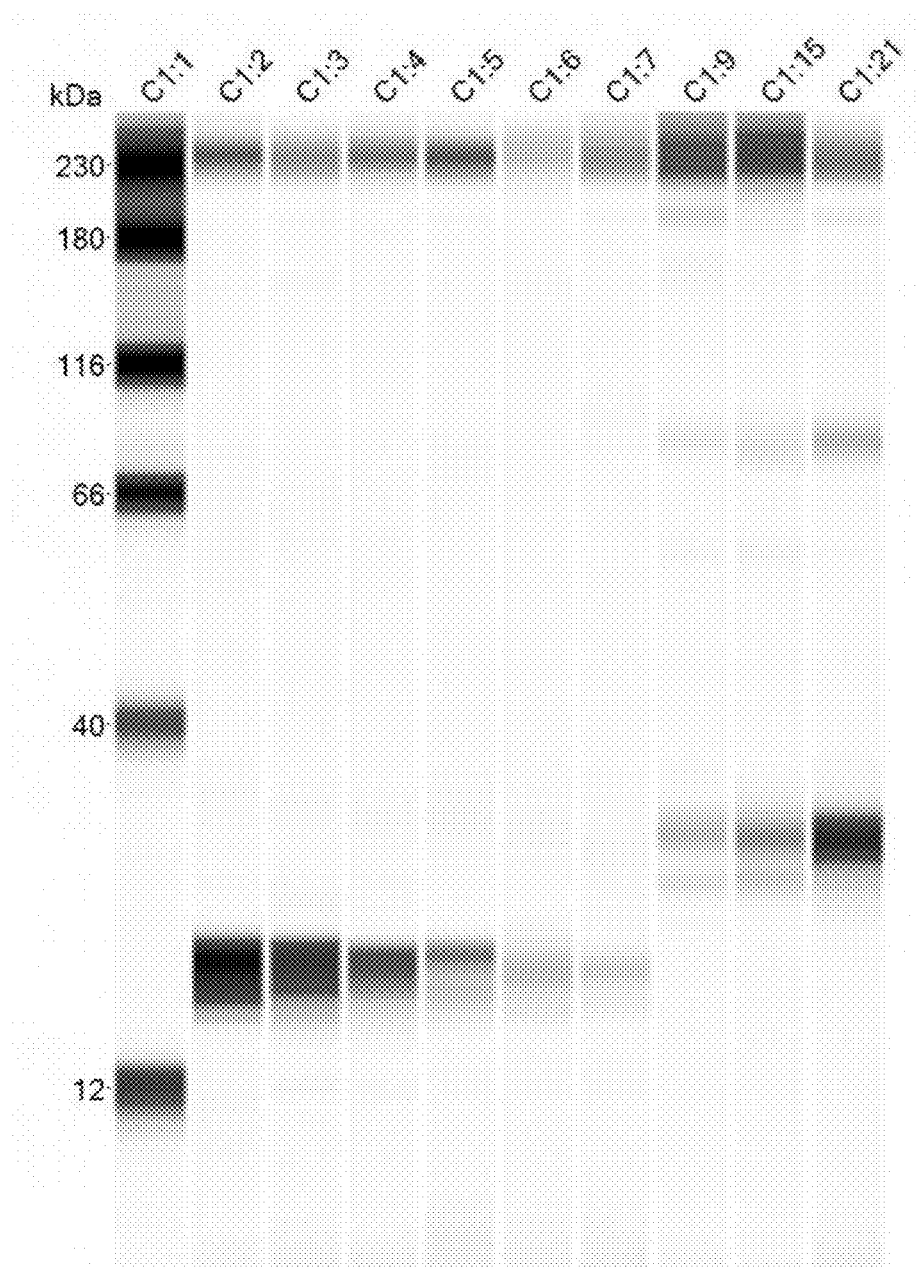
FIG. 1 pH Effects on Extractability

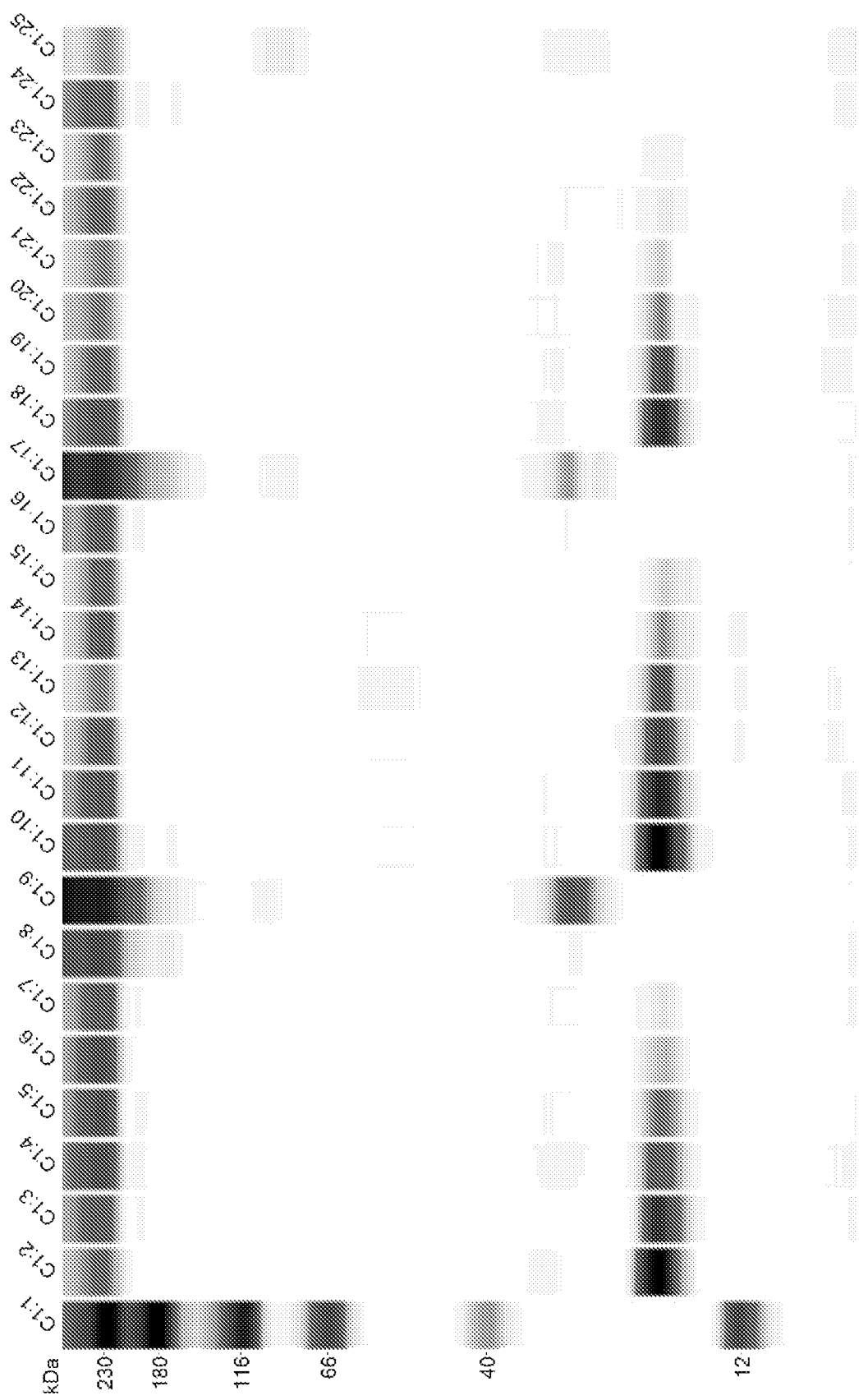
FIG. 2 Effects of Detergent and Reducing Agent on Extractability

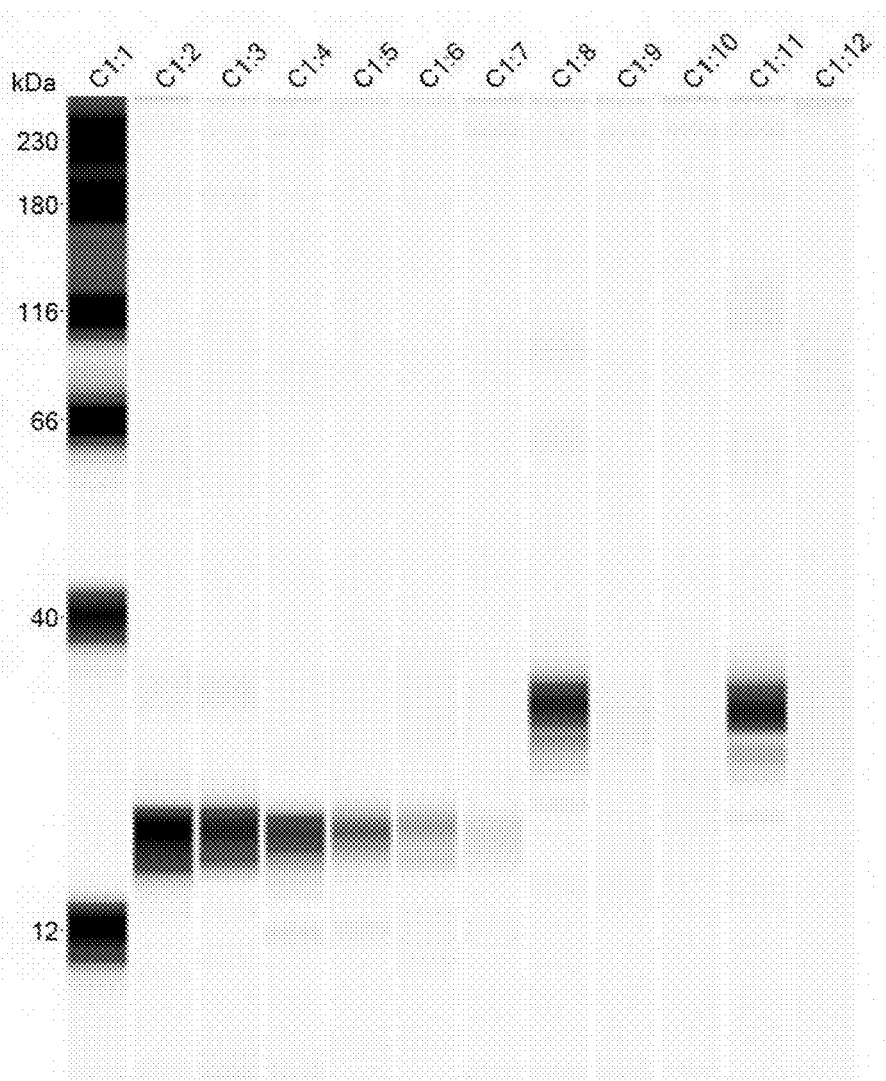
FIG. 3 Effect of MEB on protein extractability (membrane Protein 1)

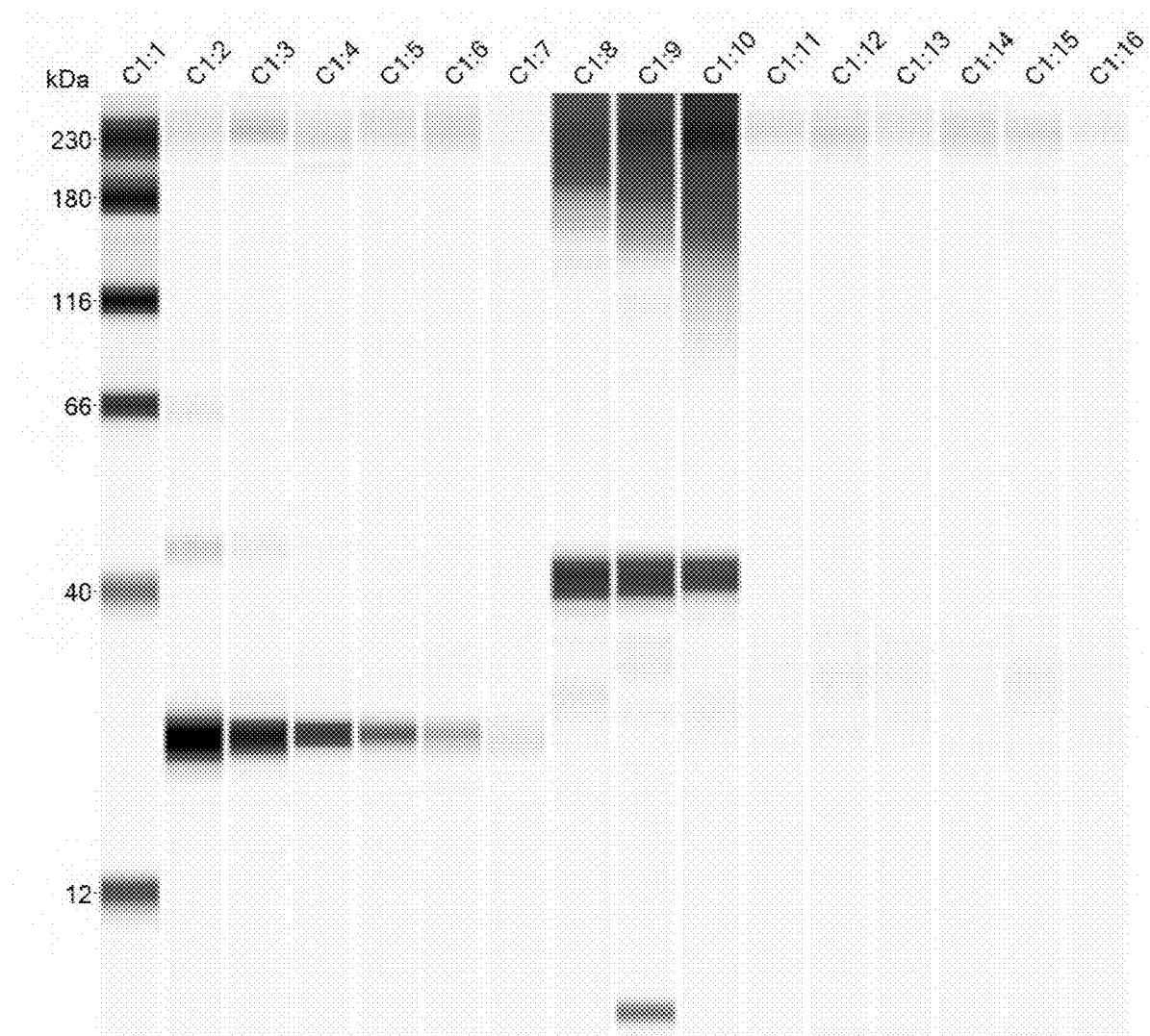
FIG. 4 Effect of MEB on protein extractability (membrane Protein 2)

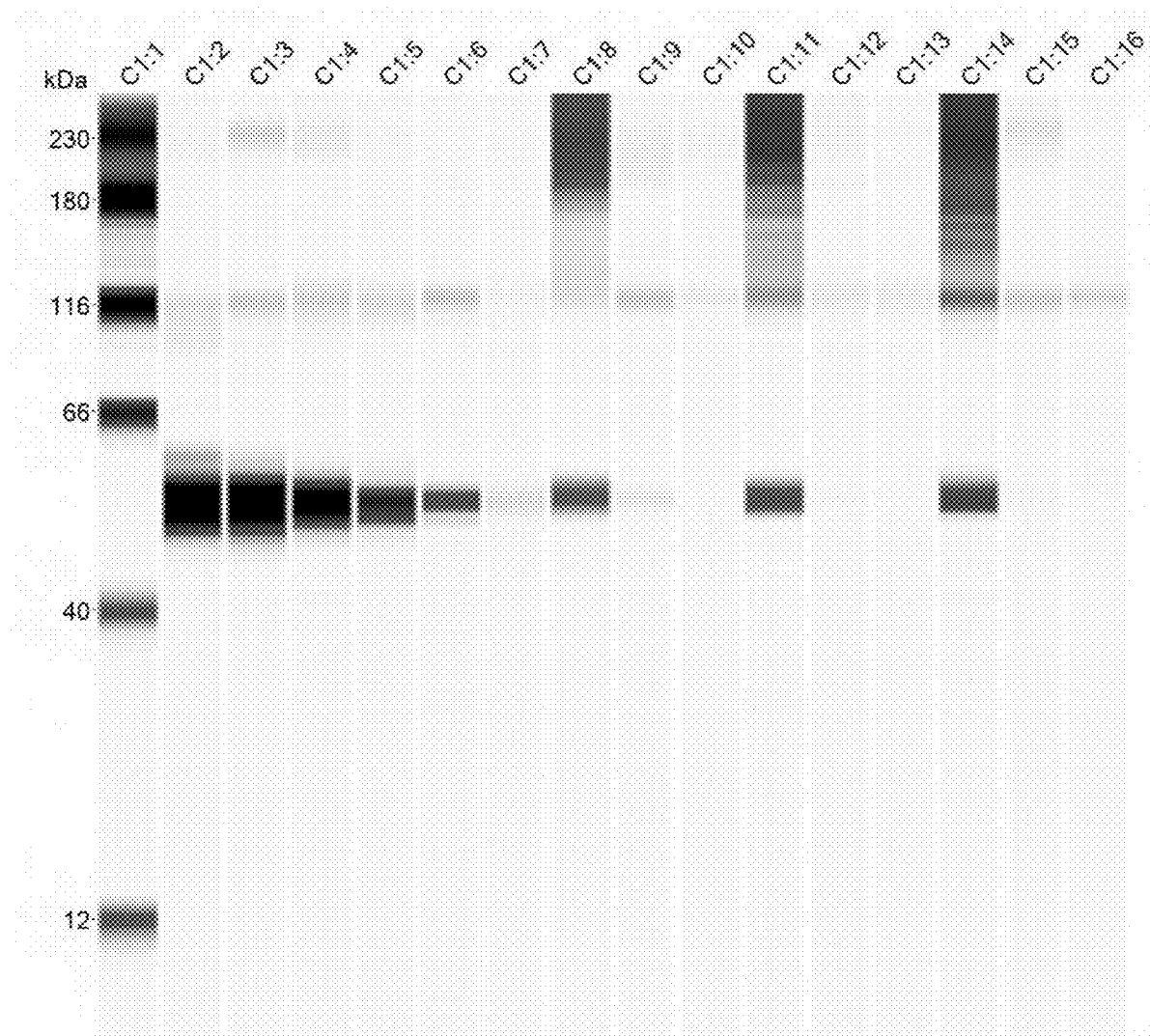
FIG. 5 Effect of MEB on protein extractability (membrane Protein 3)

FIG. 6 Effect of MEB on protein extractability (soluble Protein 4)
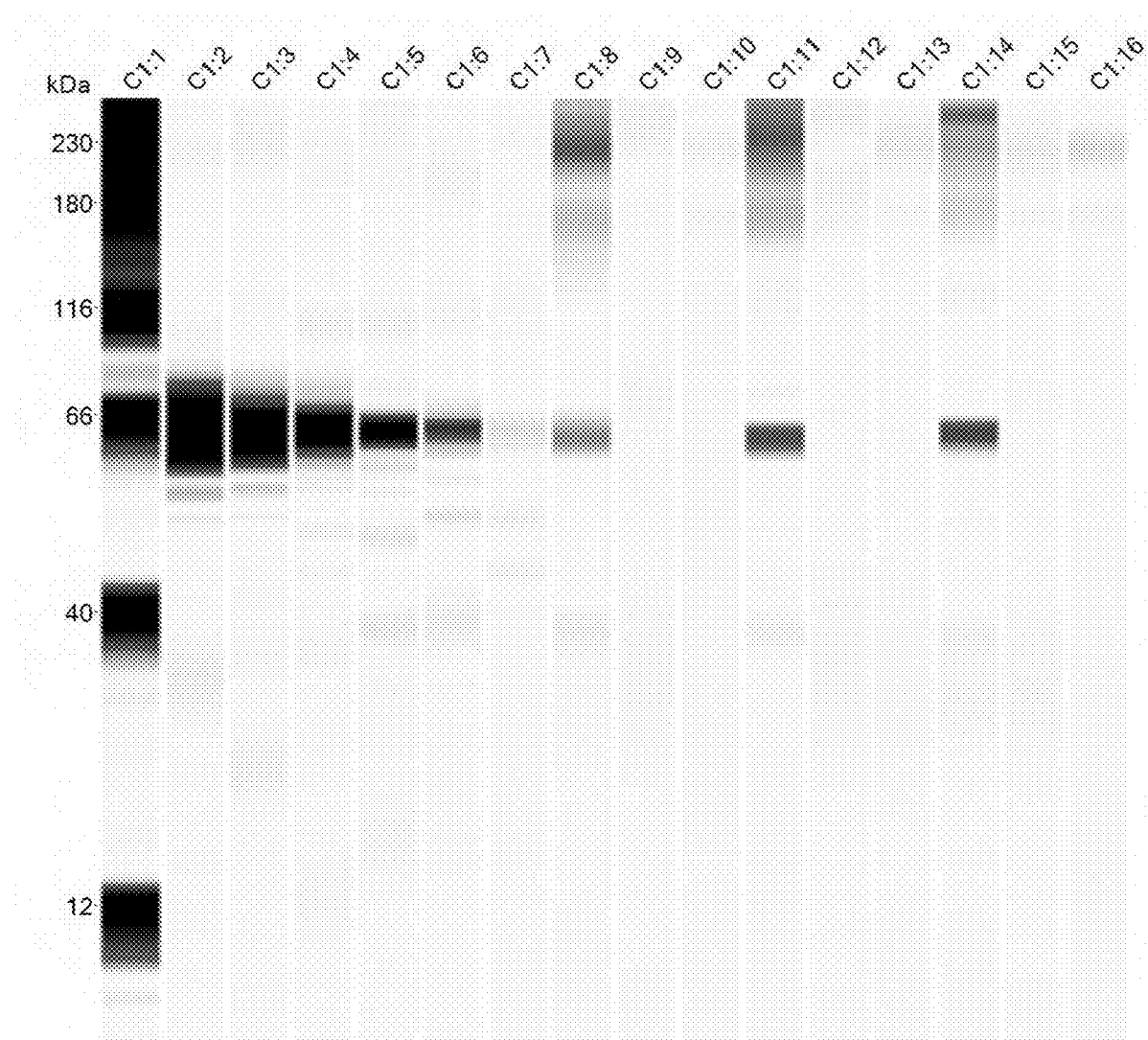

METHOD AND MEANS FOR AN ISOLATION OF MEMBRANE-BOUND PROTEINS FROM A BIOLOGICAL SAMPLE, PREFERABLY PROCESSED PLANT SEED MEAL

For the successfully and efficient extraction of intractable proteins from biological tissues and samples, it is necessary to identify optimal lysis buffer components and lysis conditions.

The most challenging tissue type encountered for the extraction of proteins is grain meal, e.g. meal derived from highly processed seed matrices of oil seed plants, for example from *Brassica* sp, like canola. The meal is a by-product of the oil extraction and can contain high quantities of proteins. The meal is highly processed by applying elevated temperature (cooking and toasting at 80-120° C.), pressure (pressing), and harsh chemical (hexane solvent extraction) conditions. The membrane-bound proteins contained in meal are denatured and are extremely difficult to be extracted using typical extraction buffers.

Quantitative immunoassays are used to generate data critical to the deregulation of agricultural biotechnology products. One of the most important aspects of a validated immunoassay method is the extractability of the analyte from a given matrix. Achieving high extractability of proteins from canola meal is very challenging due to its highly processed characteristics. Additionally, the intractable nature of membrane-bound proteins has a compounding effect on the difficulty of extractability from canola meal.

It is therefore very important to develop a method that can effectively extract the membrane proteins from biological samples, for example from plant meal.

It was found that the standard extraction buffer is insufficient to extract membrane proteins, in particular from highly processed (high temperature and high pH) plant meals, e.g. from oil seed plant meal like canola meals. Standard extraction buffers are described for example in http://www.vbcf.ac.at/fileadmin/user_upload/ProTech/SW_Buffer_compatibility.pdf and in Example 5.

Klockman et al. developed an extraction method that maximizes protein recovery without affecting the protein quality negatively (J. Agric. Food Chem., 1997, 45, 3867-3870). An isolation of proteins with an alkine dispersion solution comprising 0.4% NaOH at room temperature was described. Klockeman et. al. showed that extraction of proteins from canola meal is possible through agitation of the sample in the high pH NaOH solution at room temperature, followed by precipitation with acetic acid. While useful for downstream analysis of soluble canola proteins, this method did not lend itself to immediate and effective immunoassay analysis of proteins, specifically those that are membrane-bound.

Gerzhiva et al. concluded that despite several attempts in the past to improve the extraction efficiency of proteins from canola meal, the alkaline extraction remains most effective. The authors then investigate the effect of pH, salt addition and zeta-potential/turbidimetry analysis on protein extraction from canola meal (Food Chemistry, 2016, 243-252). They conclude that pH has the strongest effect on protein extractability and a maximum extractability was obtained at pH12 at room temperature. At this high pH the extraction is insensitive to the salt condition and the ionic strength of the buffer.

However, Gerzhiva et al as well as Klockman et al did not provide any method for the efficient extraction of membrane proteins from a biological sample, e.g. from plant meal.

The methods described in the prior art are precipitation methods, which would require resuspension and/or solubilization prior to immunoassay analysis Thus, a novel extraction method was needed to extract membrane proteins, e.g. from highly processed meal, in an efficient manner though allowing for immediate analysis of the proteins. Accordingly, the present invention provides a method for the extraction of membrane-bound proteins from biological material comprising:

Incubating the sample at an incubation temperature of 35° C. to 55° C. in a buffering reagent of pH 10 to 12.5, comprising a detergent at 0.5% to 3%.

It was found that elevated temperatures, harsh denaturants and/or detergents result in an efficient extraction of membrane-bound proteins. Accordingly, requiring an extraction method adaptable to immediate analysis, the novel extraction buffer formulation and optimized extraction conditions were developed allowing to extract effectively extract membrane-bound proteins from oil seed meal, e.g. canola meal.

The combination of a detergent and high pH was necessary to ensure high rate of extraction of membrane-bound proteins from highly processed plant seed matrices. In addition, the extraction can be performed at a warm temperature of more than 30° C. to allow solubility of the buffer components and preventing aggregation of the extracted membrane proteins.

Using this procedure in combination with a reducing agent, a very high protein extractability percentages can be achieved, e.g. up to 100%, allowing to successfully quantify levels of extracted proteins from high oil seed meal, e.g. from canola, or other highly processed plant seed matrices as well as other typical plant tissues for example seed, grain, leaf, root, or pollen. In addition, the method of the present invention is suitable for immediate analysis after a dilution to adjust or neutralize the pH for the analysis step, preferably without prior resuspension and/or solubilization of the sample.

The term "membrane protein" or "membrane-bound protein" encompasses all proteins associated with biological membranes or matrices, including but not limited to proteins in membranes of a cell, like polypeptides e.g. in cell walls or membranes of organelles, including but not limited to proteins such as transmembrane and peripheral membrane proteins; the proteins can be attached by different means, as but not limited to proteins associated with seed matrices as well as other typical plant tissues, for example grain, leaf, root, or pollen.

It was found that performing the extraction at a warm temperature improves the solubility of the buffer components while preventing aggregation of the extracted membrane proteins. The combination of a detergent, e.g. LDS, at high pH with the high temperature allowed efficient extraction. In combination with a reducing agent, e.g. TCEP, a very high, often complete extraction of membrane-bound proteins from canola meal could be achieved.

Using this procedure and achieving very high protein extractability percentages, it became possible to successfully quantify levels of extracted proteins from plant meal. Thus, the method of the present invention and the buffer of the present invention allows to successfully extract insoluble and soluble proteins from other highly processed plant seed matrices as well as other typical plant tissues such as seed, grain, leaf, root, or pollen.

Accordingly, in the method of the invention, the novel combination of lysis buffer components and extraction conditions that were identified to effectively extract membrane-bound proteins uses an optimized membrane-bound protein lysis buffer (herein "membrane extraction buffer" or "MEB") comprising high concentrations of detergent, e.g. 0.5% to 5%, at high pH, e.g. pH 10 to pH 12.0.

When extraction with this formulation is performed at high incubation temperatures, e.g. 35° C. to 55° C., membrane-bound proteins are effectively extracted and the resulting clarified extract is suited to immediate analysis, e.g. after the extracts are diluted to neutral pH before immunoblots. The extracted proteins can for example be analyzed by mass spectrometry, isoelectric focusing, 2D gel separation of proteins, proteome analysis or western blotting.

Thus, the method of the invention comprises incubating the sample in an MEB buffer comprising a detergent content of 0.5 or 1.5% to 5%, more preferably, 1.5% to 3%, most preferred around 2%. The concentration of the detergent depends on the temperature and the solubility of the detergent. Thus, the detergent and its content is selected depending on the exact temperature and pH used in the method of the invention. A soluble concentration of the detergent is used in the method of the invention.

Accordingly, the method for the extraction of membrane-bound proteins from biological material comprises incubating the sample at in a lysis buffer of pH 10 to 12.5 comprising a soluble concentration of detergent at a level of 1.5% to 5%.

Further, the present invention relates to a method for the extraction of membrane-bound proteins from biological material comprising incubating the sample at an incubation temperature of 35° C. to 55° C. in a lysis buffer MEB of pH 10 to 12.5 comprising a soluble concentration of detergent at 0.5% to 5%.

The detergent can be an ionic or non-ionic detergent, dependent on the protein and tissue type used in the sample. Examples for further detergents are TrintonX-100, NP40, C7bzO, CHAPS, Sodium Deoxycholate, LDS or SDS as described for example under http://www.vbcf.ac.at/fileadmin/user_upload/ProTech/SW_Buffer_compatibility.pdf TritonX-100 is used for example in lysis buffer at 0.5% to 3%. LysoFos Choline 12 is used for example in lysis buffer at 0.5 to 10%. NP40 is used for example in lysis buffer at 0.5% to 1%. C7Bzo is used for example in lysis buffer at 0.5% to 2%. CHAPS is used for example in lysis buffer at 0.5% to 2%. Sodium Deoxycholate is used for example in lysis buffer at 0.5% to 2%. SDS is used for example in lysis buffer at 0.5% to 2%.

The detergent can be an ionic detergent, like SDS or LDS. It is known in the art that for example SDS is less soluble at high pH and low temperature than LDS. It was found that for temperatures of the method of the invention, LDS is well soluble. Thus, he method of the invention comprises incubating the sample in an MEB buffer comprising a detergent content of 1 to 3% LDS, for example, 1.5% to 2.5% LDS, e.g. around 2% LDS.

The incubation temperature selected for the incubation in the method of the invention allows harsh extraction conditions, however, it is required that the proteins do not aggregate. Accordingly, the incubation is performed at a incubation temperature of more than 30° C., e.g. the incubation temperature is more than 35° C., e.g. 37° C. or more, 40° C. or more, 42° C. or more, 45° C. or more, 50° C. or more, 55° C. or more, however, less than 75° C., even more preferred less than 70° C., e.g. 65° C. or less, 60° C. or less, 55° C. or less, 50° C. or less, 47° C. or less, 45° C. or less, 42° C. or less, e.g. around 35° C., around 37° C., around 40° C. or around 42° C. or around 45° C., around 47° or around 50° C. or around 60° C. Accordingly, the incubation of method of the invention can be performed between 35° C. to 55° C., or between 37° C. to 50° C. or between 40° C. to 47° C.

Requiring an extraction method adaptable to immediate analysis, e.g. western blot analysis, a novel extraction buffer formulation was developed which, in combination with optimized extraction conditions, effectively extracts membrane-bound proteins from canola meal. This procedure allows for an immediate analysis of proteins using western blot methodology, e.g. only after neutralization of the buffer pH, e.g. by diluting the sample.

Further, the lysis buffer used during the incubation step of the method of the invention comprises a reducing agent. Reducing agents are well known in the art, for example, DTT (DLDithiothreitol; Clelands Reagenz), BME (beta-mercaptoethanol) or TCEP-HCL Tris (2-carboxyethyl)phosphine hydrochloride). In standard lysis buffer, the concentration of DTT is in a range of 5 to 50 mM, BME 200 mM to 1M and TCEP at 0.5 to 10 mM.

One reducing agent or a mixture of reducing agents can be used if resulting in the same reducing capacity as 5 mM to 100 mM TCEP-HCL. Preferably, the reducing capacity is equivalent to the reducing capacity of e.g. 20 mM to 70 mM TCEP-HCL, 40 mM to 60 mM TCEP-HCL, e.g. around 50 mM TCEP-HCL.

The MEB lysis buffer used in the incubation of the method of the present invention comprises for example 5 mM to 100 mM TCEP, e.g. 20 mM to 70 mM TCEP-HCL, 40 mM to 60 mM TCEP, e.g. around 50 mM TCEP. Thus, the MEB lysis buffer comprises e.g. 20 mM TCEP or more, 30 mM TCEP or more, 40 mM TCEP or more, and 100 mM TCEP or less, 80 mM TCEP or less, 70 mM TCEP or less, or 60 mM TCEP or less. In one embodiment, the content of TCEP is around 50 mM.

The MEB lysis buffer used in the method of the present invention can also comprises for example 30 to 120 nM DTT, e.g. 50 nM to 100 nM DTT.

The MEB lysis buffer used in the method of the present invention can also comprises for example 1 to 5% BME, e.g. 2% to 4% BME.

The combination of LDS as ionic detergent and TCEP as reducing agent at high pH, e.g. at approximately pH12.0, allowed a nearly complete extraction of membrane-bound proteins from canola meal. The performance of the extraction at a warm temperature supports to maintain solubility of the buffer components while preventing aggregation of the extracted membrane proteins.

Using this procedure, a very high protein extractability percentages can be achieved, e.g. up to 100%, allowing to successfully quantify levels of extracted proteins from high oil seed meal, e.g. from canola, or other highly processed plant seed matrices as well as other typical plant tissues for example seed, grain, leaf, root, or pollen.

The membrane extraction buffer MEB can comprise an appropriate pH dependent buffering agent, or a salty solution, or an aqueous solution, e.g. water. Also, the buffering components may also be omitted. Standard buffering reagents for lysis buffer are for example, Tris-CL, HEPES, CAPS, or Sodium Phosphate buffer $NaH_2PO_4/Na_2HPO_4$. Usually, the concentration of the buffering agents are: 5 to 300 mM Tris-CL, 20 to 40 mM HEPES, 10 to 40 mM Sodium phosphate ($NaH_2PO_4/Na_2HPO_4$), or 50 mM to 500 mM CAPS.

Accordingly, the method of the invention can comprise incubation in a lysis buffer MEB that comprises or does not comprise a buffering agent.

The buffer used in the incubation has a pH of between 10 to 12.5, e.g. between pH11 and pH12.5, e.g. around pH12

Preferably, the lysis buffer MEB comprises 5 to 300 mM Tris-CL, e.g. around 110 mM, around 150 mM, around 200 mM, or around 250 mM, e.g. less than 150 mM, for example 140 mM or less, e.g. 50 to 250 mM, 70 to 200 mM, 100 to 150 mM.

The lysis buffer MEB used in the method of the invention comprises in one embodiment also a viscosity agent, for example glycerol or sucrose. For example, the lysis buffer MEB used in the method of the invention comprises 5% to 30% glycerol, preferably 10 to 25% glycerol, e.g. around 20% glycerol.

Accordingly, the method of the present invention comprises incubation of the membrane protein comprising sample in a lysis buffer MEB, the lysis buffer MEB comprises:
  i. a buffering reagent at pH 10 to 12.5, and a detergent content of 0.5% to 2.5%, or,
  ii. a buffering reagent at pH 10 to 12.5, and a detergent content of 0.5% to 3%, preferably LDS or SDS, and a viscosity agent, or,
  iii. a buffering reagent at pH 10 to 12.5, a LDS content of 1.5% to 2.5%, preferably around 2% LDS, and a viscosity agent, or,
  iv. a buffering reagent at pH 10 to 12.5, a LDS content of 1.5% to 2.5%, preferably around 2% LDS, and a reducing reagent, or,
  v. a buffering reagent at pH 10 to 12.5, a LDS content of 1.5% to 2.5%, preferably around 2% LDS, and a reducing reagent, and a viscosity agent, or,
  vi. a buffering reagent at pH 10 to 12.5, a LDS content of 1.5% to 2.5%, preferably around 2%, a reducing reagent 20 to 70 mM TCEP, preferably 50 mM, and a viscosity agent glycerol, preferably at 15 to 25%, or,
  vii. a buffering reagent wherein the buffering reagent is 100 mM to 150 mM Tris-Cl, preferably 120 mM, at pH 10 to 12.5, a LDS content of 1.5% to 2.5%, a reducing reagent 20 to 70 mM TCEP, preferably 50 mM, and 10% to 20% glycerol, or
  viii. a buffering reagent, wherein the buffering reagent is around 120 mM Tris-CL, at around pH 12, a LDS content of around 2%, and a reducing reagent around 50 mM TCEP, and around 20% glycerol.

The incubation during the method of the invention takes place for an appropriate period of time: if it is too short, the extraction efficiency a suffer, if it too long, the proteins by aggregate. The incubation time at the incubation temperature is for example be between 2 min and 180 min, e.g. between 5 min and 60 min, e.g. around 5, 10 or 15 min.

The extraction is performed as single or a multiple sequential extraction, preferably the extraction is repeated three times or less, even more preferred the extraction takes place two times or less, most preferred only once.

The method of the invention allows the efficient extraction of membrane-bound proteins from biological samples, e.g. plants or parts or fractions from plants, as seed, grain, leaf, root, or pollen or cell samples. The method of the invention allows in particular the efficient extraction from plant derived meal, e.g. from oil-seed plant meal, as meal from *Brassica* sp., as *Brassica napus* meal or canola meal, or from soy meal. A method for the production of Canola defatted meal is described in Donna M. Klockeman, Romeo Toledo, and Kevin A. Sims. Isolation and Characterization of Defatted Canola Meal Protein. (1997). J. Agric. Food Chem. 45:3867-3870.

The content of the seed meal in the buffer may be 1% or more, e.g. 5% or more, 10% or more, 15% or more, 17% or more, 20% more, 25% or more, but less than 60%, e.g. 50%, 30%, 25% or less. Thus, the content of the meal in the method of the invention, may be for example between 2% and 50%, e.g. between 5 and 40%, e.g. between 10% and 20%, or between 5% and 15%.

The meal is derived e.g. form plant meal, as for example from meal from oil seed plants like *brassica* species, in particular canola. Meal like canola meal is the byproduct of the canola seed oil production.

Thus, in one embodiment, the proteins comprised in the sample are denatured. The production of seed meal, e.g. high oil plants seed oil, for example from Canola seed, requires often the use of harsh process condition. The resulting meal comprises denatured proteins. The method of the present invention also comprises the use of a denatured protein sample, e.g. a sample in which most to all proteins are denatured. For example, at least 30% or 50% of the proteins are denaturated, or at least 60%, 70% or 90% or around 100%.

Lysis buffer can also comprise a viscosity reagent. Standard viscosity reagents are Glycerol and Sucrose. Thus, the buffer used in the incubation step of the method of the invention can comprise 5% to 25% Glycerol, e.g. 10% to 20%, preferably around 20%.

Thus, in one embodiment, the meal extraction buffer (MEB) consists of 120 mM Tris, 20% glycerol, 2% LDS, and 50 mM TCEP at pH 12.0 at around 40° C. For protein extraction, it is added to canola meal and incubated at 40° C. for 5 to 15 minutes with mixing. The crude extract can then be clarified, e.g. by spinning and the supernatant is analyzed further.

The resulting clarified extract of the method of the invention is suited to immediate analysis, e.g. by mass spectrometry, Isoelectric focusing, or 2D protein separation, Western blot. Thus, in one embodiment, the method of the invention comprises a further step of spinning the sample, e.g. in a centrifuge, and transferring the supernatant to a new test tube, preferably, whereby the test tube is cooled.

Accordingly, the method of the invention also relates to a method comprising the incubation of the sample as described above, clarifying the extract from the incubation and then analyzing the proteins extracted by ELISA, Western blotting, mass spectrometry, Isoelectric focusing, or 2D protein separation, protein sequencing.

Thus, the method of the invention comprises in one embodiment, the following steps
  a. Grinding the sample,
  b. Cooling the sample, e.g. on dry ice
  c. Weighing the sample,
  d. Extracting polypeptides from the grinded and cooled sample by applying the extraction buffer MEB of the invention or the buffer MEB described for use in the method of the invention and incubating the sample at the incubation temperature of the invention, and
  e. Spinning the sample and transferring the supernatant to a new test tube, whereby the test tube is cooled.

Thus, the method of the invention comprises in one embodiment, the following steps
  a. Providing plant meal,
  b. Adding the prewarmed extraction buffer MEB of the invention or the buffer MEB as described for use in the method of the invention to the plant material, c. Grinding the sample
d. Incubate the sample at 30° C. to 45° C., preferably at around 40° C. for 1 to 15 min, preferably 2 to 5 min, more preferred for around 3 min,
e. Centrifuge the sample and transfer the supernatant to a new container,
f. Analyze the proteins in the supernatant, e.g. by western blotting, mass spectrometry, Isoelectric focusing, or 2D protein separation The method of the invention can then comprise the following further step: Performing a the quantitative analysis of the one or more polypeptides by applying one or more antibody specifically binding to a potentially membrane-bound polypeptide, wherein for example the polypeptide is a desaturase or elongase, preferably a transgenic desaturase or elongase.

Further, the present invention relates to a composition for extracting proteins. Accordingly, the novel meal extraction buffer (MEB) is herein identified to effectively extract the membrane bound proteins, e.g. from plant-derived meal. Accordingly, the present invention also relates to a novel lysis buffer MEB for the efficient extraction of membrane-bound proteins as described above for the method of the invention.

The novel meal extraction buffer (MEB) has a pH of between 10 to 12.5, e.g. between pH11 and pH12.5, e.g. around pH12

The MEB lysis buffer comprises a detergent content of 0.5 or 1.5% to 5%, more preferably, 1.5% to 3%, most preferred of around 2%. The concentration of the detergent depends on the temperature and the solubility of the detergent. Thus, the detergent and its content is selected depending on the exact temperature and pH used in the method of the invention. A soluble concentration of the detergent is used in the method of the invention.

The detergent can be an ionic or non-ionic detergent, dependent on the protein and tissue type used in the sample. Examples for further detergents are TrintonX-100, NP40, C7bzO, CHAPS, Sodium Deoxycholate, LDS or SDS as described for example under http://www.vbcf.ac.atifilead-min/user_upload/ProTech/SW_Buffer_compatibility.pdf TritonX-100 is used for example in lysis buffer at 0.5% to 3%. LysoFos Choline 12 is used for example in lysis buffer MEB at 0.5 to 10%. NP40 is used for example in lysis buffer at 0.5% to 1%. C7Bzo is used for example in lysis buffer at 0.5% to 2%. CHAPS is used for example in lysis buffer at 0.5% to 2%. Sodium Deoxycholate is used for example in lysis buffer at 0.5% to 2%. SDS is used for example in lysis buffer at 0.5% to 2%.

The detergent can be an ionic detergent, like SDS or LDS. It is known in the art that for example SDS is less soluble at high pH and low temperature than LDS. It was found that for temperatures of the method of the invention, LDS is well soluble. Thus, the MEB buffer comprising a detergent content of 1 to 3% LDS, for example, 1.5% to 2.5% LDS, e.g. around 2% LDS.

The MEB lysis buffer comprises for example one reducing agent or a mixture of reducing agents can be used if resulting in the same reducing capacity as 5 mM to 100 mM TCEP-HCL. Preferably, the reducing capacity is equivalent to the reducing capacity of e.g. 20 mM to 70 mM TCEPHCL, 40 mM to 60 mM TCEP-HCL, e.g. around 50 mM TCEP-HCL.

The MEB lysis buffer comprises in one embodiment 5 mM to 100 mM TCEP, e.g. 20 mM to 70 mM TCEP-HCL, 40 mM to 60 mM TCEP, e.g. around 50 mM TCEP. Thus, the MEB lysis buffer comprises e.g. 20 mM TCEP or more, 30 mM TCEP or more, 40 mM TCEP or more, and 100 mM TCEP or less, 80 mM TCEP or less, 70 mM TCEP or less, or 60 mM TCEP or less. In one embodiment, the content of TCEP is around 50 mM.

The MEB lysis buffer comprises for example 30 to 120 nM DTT, e.g. 50 nM to 100 nM DTT.

The MEB lysis buffer can also comprises for example 1 to 5% BME, e.g. 2% to 4% BME.

The membrane extraction buffer MEB comprise in one embodiment an appropriate pH dependent buffering agent, or a salty solution, or an aqueous solution, e.g. water. Also, the buffering components may also be omitted. Standard buffering reagents for lysis buffer are for example, Tris-CL, HEPES, CAPS, or Sodium Phosphate buffer NaH2PO4/Na2HPO4. Usually, the concentration of the buffering agents are: 5 to 300 mM Tris-CL, 20 to 40 mM HEPES, 10 to 40 mM Sodium phosphate (NaH2PO4/Na2HPO4), or 50 mM to 500 mM CAPS.

The lysis buffer MEB comprises in one embodiment also a viscosity agent, for example glycerol or sucrose. For example, the lysis buffer MEB comprises 5% to 30% glycerol, preferably 10 to 25% glycerol, e.g. around 20% glycerol.

Thus, the novel lysis buffer MEB comprises for example:
i. a buffering reagent at pH 10 to 12.5, and a detergent content of 0.5% to 2.5%, or,
ii. a buffering reagent at pH 10 to 12.5, and a detergent content of 0.5% to 3%, preferably LDS or SDS, and a viscosity agent, or,
iii. a buffering reagent at pH 10 to 12.5, a LDS content of 1.5% to 2.5%, preferably around 2% LDS, and a viscosity agent, or,
iv. a buffering reagent at pH 10 to 12.5, a LDS content of 1.5% to 2.5%, preferably around 2% LDS, and a reducing reagent, or,
v. a buffering reagent at pH 10 to 12.5, a LDS content of 1.5% to 2.5%, preferably around 2% LDS, and a reducing reagent, and a viscosity agent, or,
vi. a buffering reagent at pH 10 to 12.5, a LDS content of 1.5% to 2.5%, preferably around 2%, a reducing reagent 20 to 70 mM TCEP, preferably 50 mM, and a viscosity agent glycerol, preferably at 15 to 25%, or,
vii. a buffering reagent wherein the buffering reagent is 100 mM to 150 mM Tris-Cl, preferably 120 mM, at pH 10 to 12.5, a LDS content of 1.5% to 2.5%, a reducing reagent 20 to 70 mM TCEP, preferably 50 mM, and 10% to 20% glycerol, or
viii. a buffering reagent, wherein the buffering reagent is around 120 mM Tris-CL, at around pH 12, a LDS content of around 2%, and a reducing reagent around 50 mM TCEP, and around 20% glycerol.

In one embodiment, the buffer MEB has a temperature that is more than 35° C., e.g. 37° C. or more, 40° C. or more, 42° C. or more, 45° C. or more, 50° C. or more, 55° C. or more, however, less than 75° C., even more preferred less than 70° C., e.g. 65° C. or less, 60° C. or less, 55° C. or less, 50° C. or less, 47° C. or less, 45° C. or less, 42° C. or less, e.g. around 35° C., around 37° C., around 40° C. or around 42° C. or around 45° C., or around 47° or around 50° C. or around 60° C. Accordingly, the temperature of the buffer is for example between 35° C. to 55° C., or between 37° C. to 50° C. or between 40° C. to 47° C.

In one further embodiment, the lysis buffer MEB also comprises seed meal, e.g 1% or more, e.g. 5% or more, 10% or more, 15% or more, 17% or more, 20% more, 25% or more, but less than 60%, e.g. 50%, 30%, 25% or less. Thus, the content of the meal in the method of the invention, may be for example between 2% and 50%, e.g. between 5 and 40%, e.g. between 10% and 20%, or between 5% and 15%.

Furthermore, the lysis buffer MEB comprises biological material, e.g. derived from plants or parts or fractions from plants, as seed, grain, leaf, root, or pollen or cell samples, e.g. oil-seed plant meal, as meal from Brassica sp., as Brassica napus meal or canola meal, or soy meal.

REFERENCES

[1] Canola Council of Canada. Steps in Oil and Meal Processing. https://www.canolacouncil.org/oil-and-meal/what-is-canola/how-canola-is-processed/steps-inoil-and-meal-processing/#Pressing. (Accessed 8 Nov. 2017).
[2] Donna M. Klockeman, Romeo Toledo, and Kevin A. Sims. Isolation and Characterization of Defatted Canola Meal Protein. (1997). J. Agric. Food Chem. 45:3867-3870.

BRIEF DESCRIPTION OF THE DRAWINGS

FIG. 1 details the pH Effects on Extractability:
Lane C1:1—molecular weight ladder; Lanes C1:2-C1:7—standard curve generated with reference protein; Lance C1:9—transgenic tissue expressing Protein 1 extracted at pH 8;
Lane C1:15—transgenic tissue expressing Protein 1 extracted at pH 10; Lane C1:21—transgenic tissue expressing Protein 1 extracted at pH 12.
Meal extraction with pH 8 buffer extracted 71.3 ng/ml Protein 1, extraction with pH 10 buffer extracted 102.14 ng/ml Protein 1 (43% increase from pH 8) and extraction with pH 12 buffer extracted 174.54 ng/ml Protein 1 (71% increase from pH 10). Compared to pH 8 extraction, extraction at pH 12 resulted in 2.45-fold more extracted protein.

FIG. 2 details the Effects of Detergent and Reducing Agent on Extractability:
Lane C1:1—molecular weight ladder; Lanes C1:2-C1:7—standard curve generated with reference protein in complete MEB buffer; Lane C1:8—wildtype canola meal sample extracted in complete MEB buffer; Lane C1:9—transgenic canola meal sample extracted in complete MEB buffer; Lanes C1:10-C1:15—standard curve generated with reference protein in MEB buffer lacking TCEP (reducing agent); Lane C1:16—wildtype canola meal sample extracted in MEB buffer lacking TCEP (reducing agent); Lane C1:17—transgenic canola meal sample extracted in MEB buffer lacking TCEP (reducing agent); Lanes C1:18-C1:23—standard curve generated with reference protein in MEB buffer lacking LDS (detergent); Lane C1:24—wildtype canola meal sample extracted in MEB buffer lacking LDS (detergent); Lane C1:25—transgenic canola meal sample extracted in MEB buffer lacking LDS (detergent).

Extracted protein was quantified against corresponding standard curve. Complete MEB extracted 146.72 ng/ml Protein 1, MEB lacking reducing agent (TCEP) extracted 70.40 ng/ml Protein 1 and MEB lacking detergent (LDS) failed to extract Protein 1 out of transgenic meal samples. This result demonstrates that detergent (for example LDS) is required to extract membrane protein out of meal matrix. Reducing agent in combination with detergent and extraction at pH 12 improves extraction of membrane proteins from meal. For example, 2.1-fold more Protein 1 was extracted when TCEP was included in extraction buffer compared to no TCEP.

FIG. 3 details the effect of MEB on protein extractability (of membrane Protein 1).
Transgenic and wildtype control canola samples were extracted in complete MEB buffer to evaluate effect of MEB on extractability of membrane protein. Transgenic sample was extracted three times and extractability was assessed as the percentage of protein extracted in the first extraction. Protein extracts were kept at 40C until all samples were ready to be analyzed.
Lane C1:1—molecular weight ladder; Lanes C1:2-C1:7—standard curve generated with reference protein in MEB buffer; Lane C1:8—first extraction of transgenic canola meal sample S1 in MEB buffer; Lane C1:9—second extraction of transgenic canola meal sample S1 in MEB buffer. Lane C1:10—third extraction of transgenic canola meal sample S1 in MEB buffer; Lane C1:11—first extraction of new transgenic canola meal sample S2 in MEB buffer performed at the same time as the third extraction S1 sample; Lane C1:12—first extraction of wildtype canola meal sample in MEB buffer performed at the same time as the third extraction S1 sample. This experiment demonstrates that MEB extracts most of the Protein 1 in the first extraction (lane C1 8) (100% extractability). No protein of interest was extracted in wildtype canola meal sample (lane C1:12). In addition, we confirmed that transgenic Protein 1 was stable in MEB at 40C over the course of experiment (compare lanes C1:8 and C1:11).

FIG. 4 details the Effect of MEB on protein extractability (of membrane Protein 2). Three transgenic canola meal samples were extracted three times each in MEB. Most of the transgenic Protein 2 in all samples was extracted in the first extraction (100% extractability).
Lane C1:1—molecular weight ladder; Lanes C1:2-C1:7—standard curve generated with reference protein in MEB buffer; Lane C1:8—first extraction of transgenic canola meal sample S1 in MEB buffer; Lane C1:9—first extraction of transgenic canola meal sample S2 in MEB buffer; Lane C1:10—first extraction of transgenic canola meal sample S3 in MEB buffer; Lane C1:11—second extraction of transgenic canola meal sample S1 in MEB buffer; Lane C1:12—second extraction of transgenic canola meal sample S2 in MEB buffer; Lane C1:13—second extraction of transgenic canola meal sample S3 in MEB buffer; Lane C1:14—third extraction of transgenic canola meal sample S1 in MEB buffer; Lane C1:15—third extraction of transgenic canola meal sample S2 in MEB buffer; Lane C1:16—third extraction of transgenic canola meal sample S3 in MEB buffer.

FIG. 5 details the Effect of MEB on protein extractability (membrane Protein 3). Three transgenic canola meal samples were extracted three times each in MEB. Most of the transgenic Protein 2 in all samples was extracted in the first extraction (100% extractability).
Lane C1:1—molecular weight ladder; Lanes C1:2-C1:7—standard curve generated with reference protein in MEB buffer; Lane C1:8—first extraction of transgenic canola meal sample S1 in MEB buffer; Lane C1:9—second extraction of transgenic canola meal sample S1 in MEB buffer; Lane C1:10—third extraction of transgenic canola meal sample S1 in MEB buffer; Lane C1:11—first extraction of transgenic canola meal sample S2 in MEB buffer; Lane C1:12—second extraction of transgenic canola meal sample S2 in MEB buffer; Lane C1:13—third extraction of transgenic canola meal sample S2 in MEB buffer; Lane C1:14—first extraction of transgenic canola meal sample S3 in MEB buffer; Lane C1:15—second extraction of transgenic canola meal sample S3 in MEB buffer; Lane C1:16—third extraction of transgenic canola meal sample S3 in MEB buffer.

FIG. 6 details the Effect of MEB on protein extractability (soluble Protein 4). Three transgenic canola meal samples were extracted three times each in MEB. Most of the transgenic Protein 2 in all samples was extracted in the first extraction (100% extractability).

Lane C1:1—molecular weight ladder; Lanes C1:2-C1:7—standard curve generated with reference protein in MEB buffer; Lane C1:8—first extraction of transgenic canola meal sample S1 in MEB buffer; Lane C1:9—second extraction of transgenic canola meal sample S1 in MEB buffer; Lane C1:10—third extraction of transgenic canola meal sample S1 in MEB buffer; Lane C1:11—first extraction of transgenic canola meal sample S2 in MEB buffer; Lane C1:12—second extraction of transgenic canola meal sample S2 in MEB buffer; Lane C1:13—third extraction of transgenic canola meal sample S2 in MEB buffer; Lane C1:14—first extraction of transgenic canola meal sample S3 in MEB buffer; Lane C1:15—second extraction of transgenic canola meal sample S3 in MEB buffer; Lane C1:16—third extraction of transgenic canola meal sample S3 in MEB buffer.

EXAMPLES

Examples 1

General Extraction and Sample Preparation Procedure

Extraction buffer components (120 mM Tris, 20% glycerol, 2% LDS, and 50 mM TCEP at pH 12.0) were combined and final pH adjusted to approximately 12.0. The solution was warmed to 40° C. to improve solubility of LDS. Homogenized canola meal samples (10-50 mg) were extracted by combining an appropriate ratio of canola meal tissue to warm extraction buffer (for example 1:40-50 for included experiments) and a stainless-steel bead into a 2 mL screw cap tube. The tube containing the sample, extraction buffer, and bead were vigorously shaken for 2 minutes at 1200 rpm using a Geno/Grinder (SPEX Sample Prep, Metuchen, N.J.). The resulting sample lysate was incubated at 40° C. with vibration using an Eppendorf Thermomixer for 30 minutes. Following incubation, the lysate was centrifuged at 12,000 to 16,000 rcf for 5-15 minutes. The supernatant was aspirated and transferred to a new polyproylene tube. The supernatant was diluted as needed using extraction buffer (for example 24-fold to 60-fold for included experiments), then prepared for analysis using the ProteinSimple capillary western blot platform. Sample preparation was performed following the manufacturer's instructions provided with kit reagents. Primary antibodies specific to membrane-bound proteins 1, 2, and, 3 were utilized to detect their respective protein targets.

Quantification of extracted protein was interpolated using a standard curve prepared by fortifying extraction buffer with homologously-expressed reference standard protein. The reference standards were diluted and prepared for analysis following the same procedure as the tissues samples.

Examples 2 pH Effects on Extractability

The effects of extraction buffer pH on protein extractability from canola meal were determined by extracting three unique meal samples with buffers prepared at pH 8.0, 10.0, and 12.0. The general extraction and sample preparation procedure was otherwise followed. Extractability of the sample was determined by comparing the signal response of Protein 1 extracted with pH 12 and pH 10 buffer to the signal response of the protein extracted with pH 8 buffer.

Examples 3

Effects of Detergent and Reducing Agent on Extractability

The effects of reducing agent (TCEP) and detergent (LDS) components were evaluated by performing extractions of Protein 1 without one of these components and comparing these results to the extractability achieved using the optimized extraction buffer including all components described in the general extraction and sample preparation procedure.

Examples 4

Extractability of Membrane-Bound Proteins 1, 2, and 3 and Soluble Protein 4 from Canola Meal The extractability of membrane-bound proteins and a soluble protein from canola meal was demonstrated by extracting three unique proteins 1, 2, and 3 using the general extraction and sample preparation procedure. The level of each protein was measured from three successive extractions of transgenic (containing proteins 1, 2, and 3) canola meal samples. Extractability of each protein was expressed as the measured concentration of the protein from the first extraction with respect to the sum of the measured concentrations from all three extractions.

Example 5

Standard Extraction Buffer:
RIPA: 20 mM TrisCl pH 7.5, 150 mM NaCl, 1 mM EDTA, 1 mM EGTA, 1% NP40, 1% Sodium deoxycholate, Protease/phosphatase inhibitors cocktail Cell Lysis Buffer: 20 mM TrisCl pH 7.5, 150 mM NaCl, 1 mM EDTA, 1 mM EGTA, 1% Triton, Protease/phosphatase inhibitors cocktail SDS Lysis Buffer: 50 mM TrisCl pH 8.1.10 mM EDTA, 1% SDS IP Lysis buffer: 25 mM TrisCl pH 7.4, 150 mM NaCl, 1 mM EDTA, 1% NP40.5% glycerol T-Per: 25 mM Bicine pH 7.6, 150 mM NaCl, Proprietary detergent Cellytic MT: Bicine, unknown concentration, 150 mM NaCl, proprietary dialysable mild detergent Commercial lysates prepared in various lysis buffers: 62.5 mM TrisCl, pH 6.8, 2% SDS, 10% Glycerol.

The invention claimed is:

1. Method for the extraction of membrane-bound proteins from grain meal or plant tissue comprising: Incubating the grain meal or plant tissue in a membrane extraction buffer (MEB), the MEB having a pH of 10 to 12.5 and comprising a soluble concentration of detergent at a level of 0.5% to 5%, and a reducing agent such that the membrane-bound proteins are extracted, wherein the membrane-bound proteins comprise a desaturase or an elongase, and
    analyzing the desaturase or elongase without prior precipitation, resuspension, or solubilization.

2. The method of claim 1, wherein the MEB has a pH of 11.5 to 12.5.

3. The method of claim 1, the grain meal or plant tissue is incubated at an incubation temperature of 35° C. to 55° C.

4. The method of claim 1, wherein the MEB has a soluble concentration of an ionic detergent of 1.5 to 5%.

5. The method of claim 1, wherein the detergent comprises 1.5 to 3% LDS.

6. The method of claim 1, wherein the reducing agent comprises DTT, BME or TCEP-HCL.

7. The method of claim 1, wherein the MEB comprises one or more reducing agents equivalent to 20 mM to 70 mM TCEP.

8. The method of claim 1, wherein the reducing agent comprises 20 mM to 70 mM TCEP, 30 to 120 nM DTT, or 1 to 5% BME.

9. The method of claim 1, wherein the MEB comprises a buffering reagent.

10. The method of claim 9, wherein the buffering reagent is Tris-CL, HEPES, CAPS, and/or Sodium Phosphate buffer NaH2P04/Na2HP04.

11. The method of claim 9, wherein the buffering reagent is
   i. 5 to 300 mM Tris-CL,
   ii. 20 to 40 mM HEPES,
   iii. 10 to 40 mM Sodium phosphate (NaH2P04/Na2HP04), and/or
   iv. 50 mM to 500 mM CAPS.

12. The method of claim 1, wherein the MEB further comprises a viscosity agent.

13. The method of claim 12, wherein the viscosity agent is 10% to 25% glycerol.

14. The method of claim 1, wherein the MEB comprises a buffering reagent at pH 10 to 12.5, a LDS content of 1.5% to 2.5%, and a reducing reagent of 20 to 70 mM TCEP, wherein the buffering reagent is 100 mM to 150 mM Tris-Cl and 10% to 20% glycerol.

15. The method of claim 3, wherein the grain meal or plant tissue is incubated at the incubation temperature between 10 min. and 180 min.

16. The method of claim 1, wherein extraction is performed as a multiple sequential extraction.

17. The method of claim 1, wherein grain meal is incubated and the grain meal is defatted plant seed meal.

18. The method of claim 1, comprising the following steps:
   a. Incubating the grain meal or plant tissue in the MEB at a temperature of 35° C. to 55° C.,
   b. extracting the membrane-bound proteins,
   c. diluting the extract to adjust the pH for the analysis of the proteins, and
   d. analyzing the proteins without prior precipitation, resuspension or solubilization.

19. The method of claim 1, wherein the extracted proteins are analyzed by Western blotting, mass spectrometry, Iso-electric focusing, or 2D protein separation.

20. The method of claim 1, comprising one or more of the following steps:
   a. Grinding the grain meal
   b. Cooling the grain meal on dry ice
   c. Weighing the grain meal
   d. Extracting polypeptides from the grinded and cooled grain meal by applying an extraction buffer MEB
   e. Spinning the grain meal and transferring the supernatant to a new test tube, whereby the test tube is cooled.

21. The method of claim 1, comprising
   a. Providing grain meal,
   b. Adding the prewarmed MEB,
   c. Grinding the grain meal,
   d. Incubating the grain meal for 5 to 15 min. at 30° C. to 45° C.,
   e. Centrifuging the grain meal and transferring the supernatant to a new container, and
   f. Analyzing the supernatant.

22. The method of claim 1, comprising the quantitative analysis of the one or more polypeptides by applying one or more antibody specifically binding to a membrane-bound polypeptide.

23. The method of claim 1, wherein the polypeptide is a transgenic desaturase or transgenic elongase.

24. The method of claim 1, wherein plant tissue is incubated and the plant tissue is selected from the group consisting of seed, grain, leaf, root, and pollen.

* * * * *